(12) United States Patent
Min

(10) Patent No.: US 10,959,837 B2
(45) Date of Patent: Mar. 30, 2021

(54) HUMAN BODY IMPLANT DEVICE

(71) Applicant: TODOC Co., Ltd., Seoul (KR)

(72) Inventor: Kyou Sik Min, Gyeonggi-do (KR)

(73) Assignee: TODOC Co., Ltd., Seoul (KR)

( * ) Notice: Subject to any disclaimer, the term of this patent is extended or adjusted under 35 U.S.C. 154(b) by 86 days.

(21) Appl. No.: 15/781,133

(22) PCT Filed: Dec. 2, 2016

(86) PCT No.: PCT/KR2016/014141
§ 371 (c)(1),
(2) Date: Jun. 3, 2018

(87) PCT Pub. No.: WO2017/095198
PCT Pub. Date: Jun. 8, 2017

(65) Prior Publication Data
US 2018/0353289 A1    Dec. 13, 2018

(30) Foreign Application Priority Data

Dec. 4, 2015    (KR) .......................... 10-2015-0171911

(51) Int. Cl.
*A61F 2/18*       (2006.01)
*H04R 25/00*   (2006.01)
(Continued)

(52) U.S. Cl.
CPC .............. *A61F 2/18* (2013.01); *A61N 1/0541* (2013.01); *A61N 1/36038* (2017.08);
(Continued)

(58) Field of Classification Search
CPC ............ A61N 1/36038; A61N 1/37518; A61N 1/0541; H04R 25/505; H04R 25/554; H04R 2225/67
See application file for complete search history.

(56) References Cited

U.S. PATENT DOCUMENTS

| | | | |
|---|---|---|---|
| 4,532,930 A * | 8/1985 | Crosby | .............. A61N 1/36036 607/57 |
| 2004/0172118 A1* | 9/2004 | Gibson | ................ A61N 1/0541 607/137 |

(Continued)

FOREIGN PATENT DOCUMENTS

| KR | 10-2009-0108373 | 10/2009 |
|---|---|---|
| KR | 10-2012-0002524 | 1/2012 |

(Continued)

OTHER PUBLICATIONS

Supplementary European Search Report and the European Search Opinion dated May 31, 2019 From the European Patent Office Re. Application No. PCT/KR2016014141. (7 Pages).

(Continued)

*Primary Examiner* — Carrie R Dorna

(57) ABSTRACT

There is disclosed a human body implant device including a first unit including a transmission unit, and a second unit configured to communicate with the first unit, wherein the second unit includes a second package including a reception unit configured to receive power or an electrical signal from the transmission unit, a first package configured to generate a stimulation signal in response to the electrical signal, a connector configured to electrically connect the first package and the second package, and a cover configured to package the first package, the second package, and the connector.

7 Claims, 15 Drawing Sheets

(51) Int. Cl.
*A61N 1/36* (2006.01)
*A61N 1/372* (2006.01)
*A61N 1/05* (2006.01)
*H01Q 1/27* (2006.01)
*A61N 1/375* (2006.01)
*A61N 1/378* (2006.01)

(52) U.S. Cl.
CPC ......... *A61N 1/37229* (2013.01); *H01Q 1/273* (2013.01); *H04R 25/00* (2013.01); *H04R 25/606* (2013.01); *A61N 1/3758* (2013.01); *A61N 1/3787* (2013.01); *H04R 25/505* (2013.01); *H04R 2225/67* (2013.01)

(56) References Cited

U.S. PATENT DOCUMENTS

| | | |
|---|---|---|
| 2005/0015133 A1 | 1/2005 | Ibrahim et al. |
| 2009/0023976 A1 | 1/2009 | Cho et al. |
| 2011/0144749 A1 | 6/2011 | Kim, I et al. |
| 2011/0224789 A1 | 9/2011 | Griffith |
| 2012/0316454 A1 | 12/2012 | Carter |

FOREIGN PATENT DOCUMENTS

| | | |
|---|---|---|
| KR | 10-1393186 | 5/2014 |
| WO | WO 2010/0911174 | 8/2010 |
| WO | WO 2015/030734 | 3/2015 |
| WO | WO 2017/095198 | 6/2017 |

OTHER PUBLICATIONS

International Search Report and the Written Opinion dated Feb. 20, 2017 From the International Searching Authority Re. Application No. PCT/KR2016/014141 and Its Translation of Search Report Into English. (12 Pages).

* cited by examiner

FIG. 12(a)
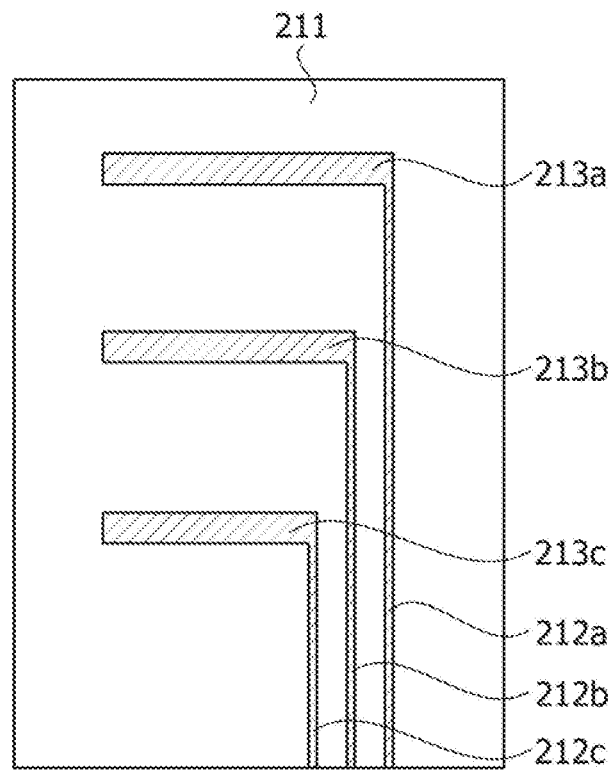
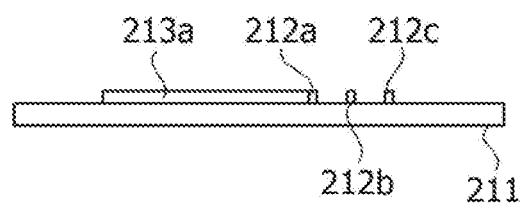
FIG. 12(b)

FIG. 13(a)
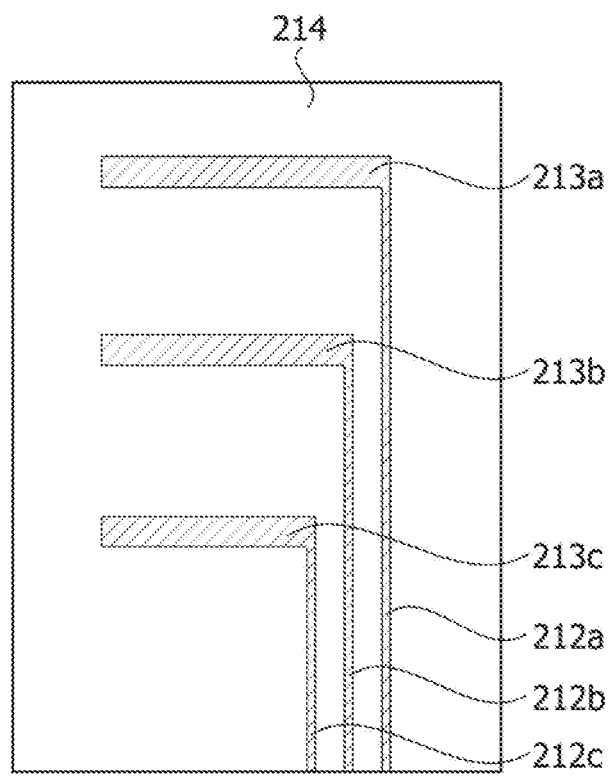
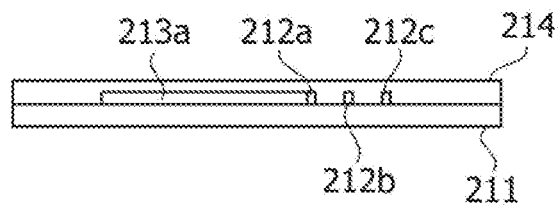
FIG. 13(b)

FIG. 15(a)
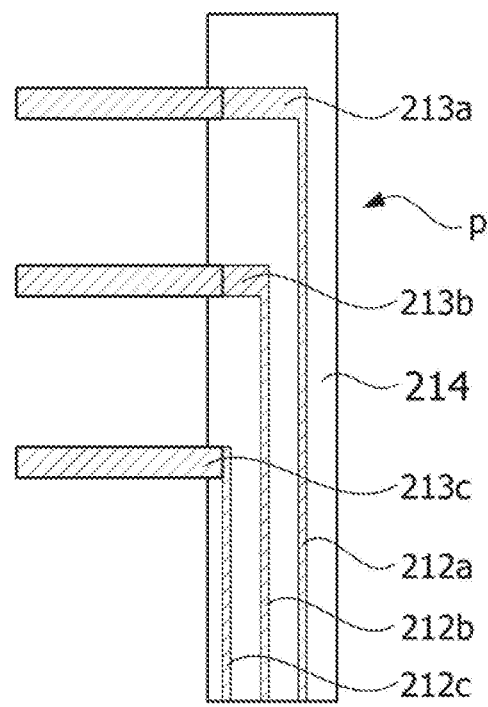
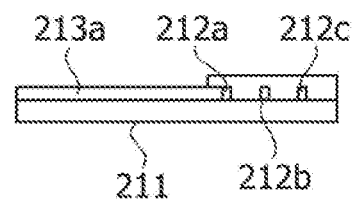
FIG. 15(a)

HUMAN BODY IMPLANT DEVICE

RELATED APPLICATIONS

This application is a National Phase of PCT Patent Application No. PCT/KR2016/014141 having International filing date of Dec. 2, 2016, which claims the benefit of priority of Korean Patent Application No. 10-2015-0171911 filed on Dec. 4, 2015. The contents of the above applications are all incorporated by reference as if fully set forth herein in their entirety.

TECHNICAL FIELD AND BACKGROUND OF THE INVENTION

Embodiments relate to a human body implant device.

Many medical devices have been developed to help people who have lost a specific function, either congenital or acquired. As such medical devices, human body implant devices including nerve assist devices have also been developed. As one of the human body implant devices, the cochlear implant system, which stimulates auditory nerves of people who have functioning auditory nerves with electricity to help the people sense sound, has been recognized as the most efficient device among the nerve assist devices that have been developed thus far, and such cochlear implants are increasing every year.

The cochlear implant system may include an external device provided outside the body and an internal device provided inside the body.

The external device serves to receive sound from outside the human body and convert the received sound into an electrical signal, and includes a microphone (sender), a speech sound processor (language synthesizer), and a transmitting antenna (transmitter). In this case, the microphone and the transmitting antenna may be combined with a headset.

The internal device serves to stimulate the auditory nerve using signals transmitted from the external device, and includes a receiver and an electrode for reception and stimulation.

The cochlear implant system transmits an acoustic signal transmitted from the microphone attached to a part outside the human body to the auditory nerve fibers through the electrode implanted in the cochlear, without passing through the eardrum or the auditory ossicles, by converting physical vibration of the acoustic signal into an electrical signal through processes of amplification, filtering, and the like by the external speed sound processor.

The external device of the cochlear implant system consumes power to drive the microphone, the speech sound processor, and the like, and the internal device also requires power for driving the receiver. In a conventional cochlear implant system, an internal device provided inside the body includes an internal coil configured to supply power through radio frequency (RF) communication with an external coil provided outside the body.

In the conventional cochlear implant system, the internal device that is inserted into the body is inserted into the scalp at a central portion of a side of the head, and the external device is distributed across the outside of the scalp.

However, in such a configuration, since use of the cochlear implant system is easily recognizable by visual inspection, a user who does not want to let others know about his or her use of the cochlear implant system may be dissatisfied or mentally bothered.

Further, since the components of the cochlear implant system are exposed as they are, the exterior of the cochlear implant system is not preferable, and thus improvement is required.

That is, since areas where a user can wear the cochlear implant system are very limited, the degree of freedom of wearing the cochlear implant system is low, and thus improvement is required.

Further, the conventional electrode has problems in that the cost and time are increased and the yield is decreased because a platinum electrode and a wire are manually aligned and silicone-molded. Further, there is a problem in that current stimulation is relatively low due to a small electrode area.

SUMMARY OF THE INVENTION

Embodiments may provide a human body implant device capable of providing an improved degree of freedom of wearing the same.

Further, a human body implant device that is easy to manufacture may be provided.

Further, a human body implant device in which an electrode area is widened so that a relatively high current stimulation is applicable may be provided.

Further, a human body implant device capable of injecting drugs while providing electrical stimulation may be provided.

Technical Solution

A human body implant device according to an embodiment includes a first unit including a transmission unit, and a second unit configured to communicate with the first unit, wherein the second unit includes a second package including a reception unit configured to receive power or an electrical signal from the transmission unit, a first package configured to generate a stimulation signal in response to the electrical signal, a connector configured to electrically connect the first package and the second package, and a cover configured to package the first package, the second package, and the connector.

The transmission unit may include a first coil, and the reception unit may include a second coil.

The first package may include a circuit configured to process the electrical signal and generate the stimulation signal, and an electrode array including a plurality of power sources to which a current signal in response to the stimulation signal is applied.

The connector may electrically connect the reception unit and the circuit.

The connector may include a wire configured to electrically connect the reception unit and the circuit.

The first unit may include a sender configured to sense an acoustic signal, a voice processor configured to convert the acoustic signal into an electrical signal, and a transmitter configured to transmit the electrical signal.

The human body implant device may include an aligner including the first coil.

The aligner may include at least one of a sender configured to sense an acoustic signal, a voice processor configured to convert the acoustic signal into an electrical signal, and a transmitter configured to transmit the electrical signal.

The electrode array may include a substrate extending in a first direction, a plurality of lead wires disposed on the substrate, a mold member configured to cover the lead wires, and a plurality of electrodes disposed on an outer peripheral surface of the mold member, wherein the plurality of electrodes may each be electrically connected to the plurality of lead wires, and the plurality of electrodes may be disposed to be spaced apart from each other in the first direction.

The electrodes may have both ends inserted and fixed into the mold member, and one end of the electrodes may be electrically connected to the lead wires.

The human body implant device may include a first section in which the electrodes are disposed, and a second section in which the electrodes are spaced apart from each other in the first direction, and a ratio between widths of the first section and the second section in the first direction may be in a range of 1:0.2 to 1:1.5.

The electrode array may include a substrate extending in a first direction, a plurality of lead wires disposed on the substrate, a mold member configured to cover the substrate and the lead wires, and a plurality of electrodes electrically connected to the lead wires via the mold member, wherein the mold member may include a flow path disposed therein and extending in the first direction, and a plurality of holes connected to the flow path.

Advantageous Effects

According to an embodiment of the present invention, since the first package and the second package can be disposed independently from each other while being electrically connected by the connector, various positions may be selected as a position of the second package.

Therefore, the second package can be located at a position that makes the second package difficult to be identified by others through visual inspection, or a position that allows the second package to form a smoother operational relationship with the first unit.

In this way, since the first unit can be provided so as not to be fully exposed to the outside, or various shapes can be applied as the shape of the first unit so that a user is less aversive about the shape, a user who does not want to let others know about his or her use of the human body implant device can be satisfied, and the user can have an improved degree of freedom of wearing the human body implant device.

Further, the electrode array can be easily manufactured by injecting the mold member to the electrode.

Further, due to a widened electrode area, a relatively high stimulation can be applied.

Further, drugs can be injected into the human body.

The advantageous effects of the present invention are not limited to the above-mentioned advantageous effects, and it should be understood that the advantageous effects of the present invention include all advantageous effects that may be inferred from the detailed description of the present invention below or the configuration of the invention defined in the claims below.

BRIEF DESCRIPTION OF THE SEVERAL VIEWS OF THE DRAWINGS

FIGS. 12(*a*), 12(*b*), 13(*a*), 13(*b*), 14(*a*), (14*b*), 15(*a*), 15(*b*) 16, 17, 18, 19, 20 and 21 are views showing a process of manufacturing an electrode array.

DESCRIPTION OF SPECIFIC EMBODIMENTS OF THE INVENTION

Figure 1:
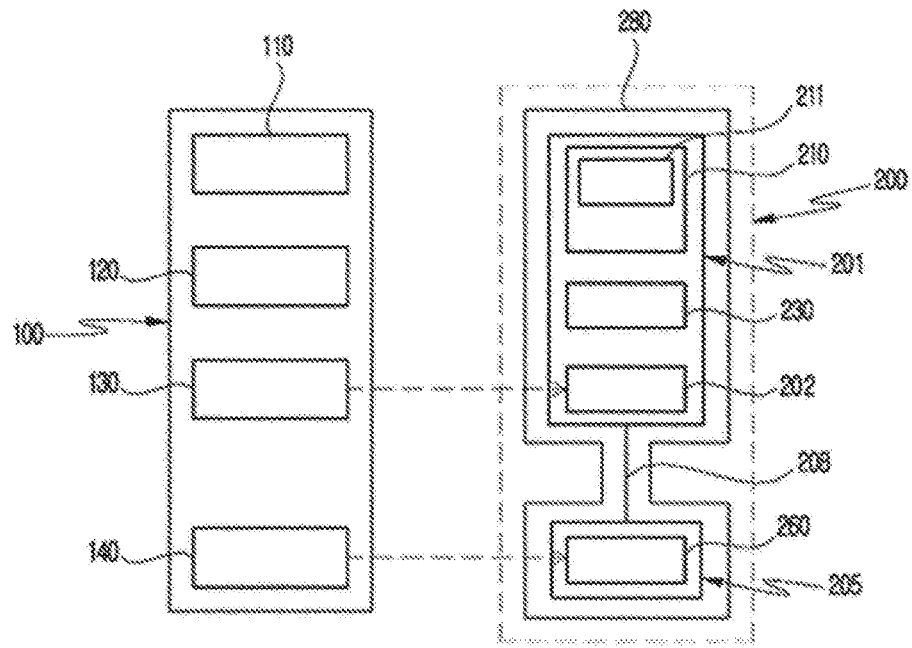
FIG. 1 is a block diagram illustrating a human body implant device according to an embodiment of the present invention.

Hereinafter, the present invention will be described with reference to the accompanying drawings. However, the present invention may be implemented in various other forms, and thus is not limited to the embodiments described herein. To clearly describe the present invention, parts unrelated to the description have been omitted from the drawings, and like elements are denoted by like reference numerals throughout.

Throughout the specification, when a certain part is described as being "connected" to another part, a case in which the certain part is "indirectly connected" to the other part via another element therebetween as well as a case in which the certain part is "directly connected" to the other part are included. When a certain part is described as "including" a certain element, this signifies that the certain part may also include another element rather than excluding the other element unless particularly described otherwise.

The following embodiments are merely examples for giving the description, and the scope of the present invention is not limited thereto. Configurations of each embodiment may be combined with each other and constitute a new embodiment. Although not described herein, specific configurations that may be easily substituted and/or changed by those of ordinary skill in the art may be applied to the embodiments herein. Further, specific configurations of the embodiments herein should be understood as illustrative.

Hereinafter, embodiments of the present invention will be described in detail with reference to the accompanying drawings.

Figure 2:
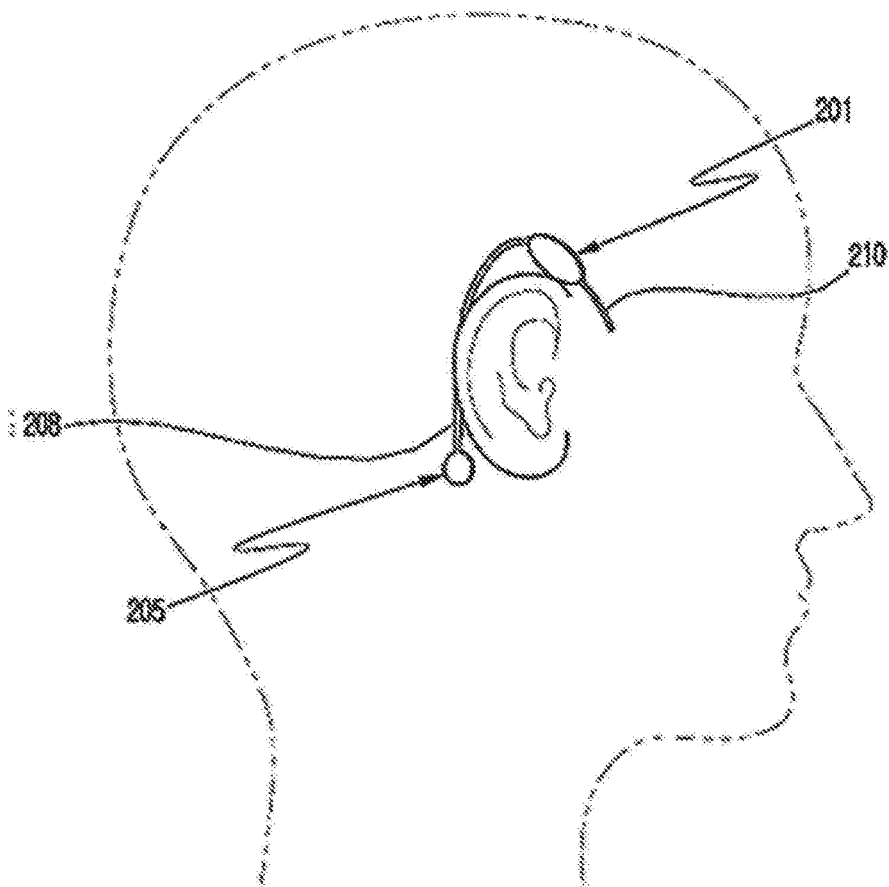
FIGS. 2 and 3 are exemplary views illustrating examples in which a second unit of the human body implant device according to the embodiment of the present invention is applied to the human body.
Figure 3:
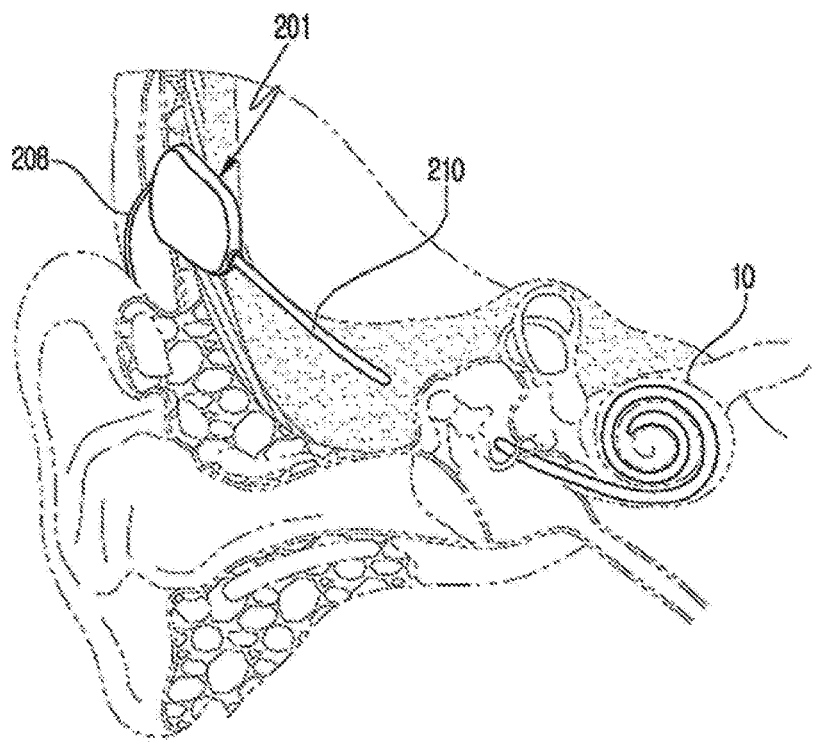
Figure 4:
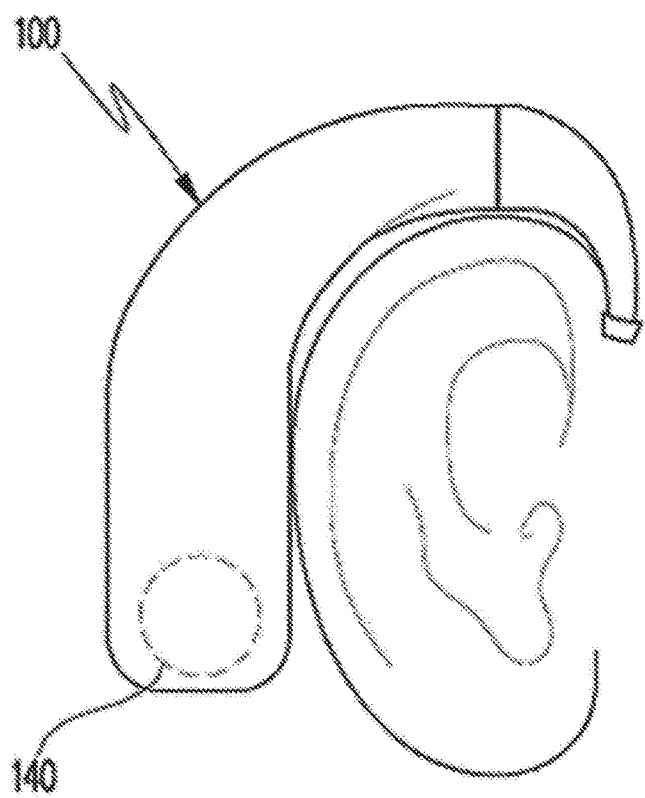
FIG. 4 is an exemplary view illustrating an example in which a first unit of the human body implant device according to the embodiment of the present invention is applied to the human body.

FIG. 1 is a block diagram illustrating a human body implant device according to an embodiment of the present invention, FIGS. 2 and 3 are exemplary views illustrating examples in which a second unit of the human body implant device according to the embodiment of the present invention is applied to the human body, and FIG. 4 is an exemplary view illustrating an example in which a first unit of the human body implant device according to the embodiment of the present invention is applied to the human body.

Referring to FIGS. 1 to 4, a human body implant device according to an embodiment may include a first unit 100 and a second unit 200. Hereinafter, for convenience of description, a cochlear implant system, which is one of the human body implant devices, will be described as an example, but the human body implant device is not necessarily limited thereto.

The first unit 100 may convert an acoustic signal into an electrical signal, and include a first coil 140 provided outside the skin and configured to supply power.

The second unit 200 may be inserted into the skin, receive the electrical signal from the first unit 100, and stimulate auditory nerve fibers in a cochlea 10.

The second unit 200 may include a first package 201, a second package 205, and a connector 208.

The first package 201 may include a circuit 230 configured to process a signal received from the first unit 100 and generate a stimulation signal, and an electrode array 210 having a plurality of electrodes 211 configured to stimulate auditory nerve fibers with a current signal in response to the stimulation signal transmitted from the circuit 230.

The second package 205 may be disposed independently from the first package 201, and include a second coil 260 configured to receive power from the first coil 140.

The connector 208 may electrically connect the first package 201 and the second package 205.

According to an embodiment, since the first package 201 and the second package 205 may be disposed independently from each other while being electrically connected, various positions may be selected as a position of the second package 205.

The second package 205 may be located at a position that makes the second package 205 difficult to be identified by others through visual inspection, or a position that allows the second package 205 to form a smoother operational relationship with the first unit 100.

In this way, since the first unit 100 can be provided so as not to be fully exposed to the outside, or various shapes can be applied as the shape of the first unit 100 so that a user is less aversive about the shape, a user who does not want to let others know about his or her use of the cochlear implant system can be satisfied, and the user can have an improved degree of freedom of wearing the cochlear implant system.

Although the cochlear implant system is described as an example in the embodiment of the present invention, the human body implant device is not limited thereto. For example, the second unit 200 may also provide an electrical signal to a different organ of the human body.

For example, the second unit 200 may also supply an electrical signal to the brain of the human body. Even in this case, since the first package 201 and the second package 205 may be disposed independently from each other, the position of the second package 205 may be different from that of the first package 201.

Therefore, even when the first package 201 is disposed at a head portion to provide an electrical signal to the brain, the second package 205 configured to receive power from the outside may be disposed at a different portion, e.g., a portion that is less exposed to the outside, such as an auricle or an auditory pit.

Likewise, even when the first package 201 is disposed near an organ in the body such as the heart, the lung, or the liver, the second package 205 may be disposed at a different position. Therefore, since the user may carry the first unit 100 regardless of the position of an organ that requires electrical stimulation, the user's degree of freedom of wearing the human body implant device may be significantly improved.

That is, although the cochlear implant system is mainly described as an exemplary embodiment of the present invention, the human body implant device is not limited thereto and includes all human body implant devices capable of being inserted into the human body and providing electrical stimulation.

The first unit 100 may be provided outside the skin. That is, the first unit 100 may be mounted outside the body without being implanted in the body.

The first unit 100 may include a sender 110, a voice processor 120, a transmitter 130, and the first coil 140.

The sender 110 may sense an acoustic signal. The acoustic signal may include a voice signal or a sound signal.

The voice processor 120 may receive the acoustic signal sensed by the sender 110 and convert the received acoustic signal into an electrical signal. The voice processor 120 may include a speech processor.

The transmitter 130 may receive the electrical signal from the voice processor 120 and transmit the received electrical signal.

The first coil 140 may supply power.

The transmitter 130 may be omitted. That is, the first unit 100 may not include a separate transmitter 130. In this case, the first unit 100 may receive the electrical signal from the voice processor 120 and transmit the received electrical signal to the second unit 200 while power is being transmitted thereto through the first coil 140.

The first unit 100 may include a power source (not illustrated). The power source is a configuration for supplying power to the first unit 100, and may include a replaceable battery, a rechargeable battery, or the like.

The power source may also receive power from the outside and store the received power. For example, the power source may include a capacitive element such as a capacitor. The capacitive element may receive power from an external power source via a wire and store the received power, or wirelessly receive power from an external power source through the first coil 140 of the first unit 100.

For example, the first coil 140 may wirelessly receive power from a coil of an external power source through electromagnetic induction and store the received power in a capacitive element in a charging mode, and wirelessly transmit power in the capacitive element to the second coil 260 of the second unit 200.

Here, although the electromagnetic induction phenomenon may be used for transmitting power through the coil, embodiments are not limited thereto, and other wireless power transmission techniques may also be used.

The second unit 200 may be inserted into the skin. In other words, the second unit 200 may be inserted into the skin, e.g. the subcutaneous layer, or may be implanted in the body.

The second unit 200 may include the first package 201, the second package 205, and the connector 208.

First, the first package 201 may have a receiver 202, the circuit 230, and the electrode array 210.

The receiver 202 may receive a signal from the second package 205. For example, when the second package 205 receives a signal along with power from the first unit 100 through the second coil 260, the second package 205 may extract the signal and transmit the signal to the receiver 202 through the connector 208. When the first coil 140 of the first unit 100 transmits power to the second coil 260 of the second unit 200, the first coil 140 may also transmit a data signal for electrical stimulation, along with a power signal, to the second coil 260. For example, the first coil 140 may vary an amplitude or phase of a power signal and transmit a data signal along with the power signal.

Alternatively, the receiver 202 may directly receive a signal from the transmitter 130 of the first unit 100. The transmitter 130 and the receiver 202 may communicate using various communication techniques which are not limited to a specific communication technique. A data signal may also be transmitted separately from a power signal through a separate communicator or a separate frequency which is not described above.

The circuit 230 may process the signal received by the receiver 202 and generate a stimulation signal. The circuit 230 may have an integrated chip (IC) for generating a stimulation signal.

The electrode array 210 may have one or more electrodes 211. The electrodes 211 may be provided at an insulating layer (not illustrated), and the insulating layer may be formed to be thin so that the insulating layer is insertable into the cochlea 10.

The electrodes 211 may stimulate auditory nerve fibers in the cochlea 10 with a current signal in response to the stimulation signal transmitted from the circuit 230, and may also collect, detect, and record a biometric signal from the auditory nerve fibers.

The second package 205 may be disposed independent of the first package 201 and may have the second coil 260. The second coil 260 may receive power from the first coil 140 using the electromagnetic induction method, and the power received by the second coil 260 may be used as a power source of each component of the first package 201. For example, when a current is applied to the first coil 140 and a magnetic field is formed around the coil, a magnetic field may be formed at the second coil 260 as a result, and a current may flow to the second coil 260 through the magnetic field. Alternatively, the second coil 260 may also receive power from the first coil 140 through radio frequency (RF) communication.

The connector 208 may electrically connect the first package 201 and the second package 205. The connector 208 may be in the form of a wire and be flexible. Accordingly, the second package 205 may be implanted in various positions spaced apart from the first package 201. Although, preferably, a copper wire may be used as the connector 208, embodiments are not limited thereto, and other conductive materials such as gold and platinum may also be used.

The length of the connector 208 may be in the range of 1 cm to 10 cm. When the length is smaller than 1 cm, it is difficult to arrange the second package at a desired position, and when the length is larger than 10 cm, the connector is too long such that the size of the connector is increased.

The second unit 200 may include a cover 280. The cover 280 may seal and package the first package 201, the second package 205, and the connector 208. The cover 280 may include a polymer-based material, preferably, a liquid crystal polymer. For example, the cover 280 may be a liquid crystal polymer film. The cover 280 may package the second unit 200 so that the second unit 200 is sealed and prevent body fluid from entering the second unit 200.

According to an embodiment of the present invention, the second coil 260 may be provided in the scalp behind the ear. For example, the second coil 260 may be located below the temporal bone and may be inserted and implanted in the mastoid process that is disposed below a rear side of the auricle when viewed from the outside.

The first package 201 may be formed to be hung on the ear. When the first package 201 is mounted to be hung on the ear, the second package 205 may be disposed at a lower portion of the auricle as illustrated in FIG. 2. In this case, the first coil 140 of the first unit 100 may be disposed at a position corresponding to the second coil 260 so that the first coil 140 is aligned in place with the second coil 260.

In this way, communication may be stably performed between the first coil 140 and the second coil 260. When the first coil 140 and the second coil 260 are disposed to be aligned in place as described above, a coupling coefficient between the coils may be increased such that efficient power transmission and/or data communication is possible, and a magnetic field region may be minimized such that an influence of the magnetic field on the human body is minimized.

According to the present embodiment, since the second package 205 of the second unit 200 may be disposed independently from the first package 201, even when the first package 201 is located in the vicinity of the cochlea 10 due to the characteristic of having the electrode array 210 inserted into the cochlea 10, the second package 205 may be freely installed at an appropriate position. Therefore, when the first package 201 has a shape capable of being hung on the ear, the second coil 260 of the second package 205 may be disposed to correspond to the position of the first coil 140 of the first unit 100.

The first unit 100 may be in the form of a wearable device capable of being hung on the ear without a separate attaching means, but embodiments are not limited thereto. For example, the first unit 100 may be attached to the human body using an adhesive tape, or the first unit 100 may include a magnet therein and be fixed to the second unit 200 by a magnetic force. The first unit 100 may also include an electromagnet therein. In this case, as the first unit 100 is switched on, the electromagnet may be operated, and the first unit 100 may be fixed to the human body by a magnetic force, and when the first unit 100 is switched off, the electromagnet may be deactivated and be detached, and the first unit 100 may be detached from the human body.

Figure 5:
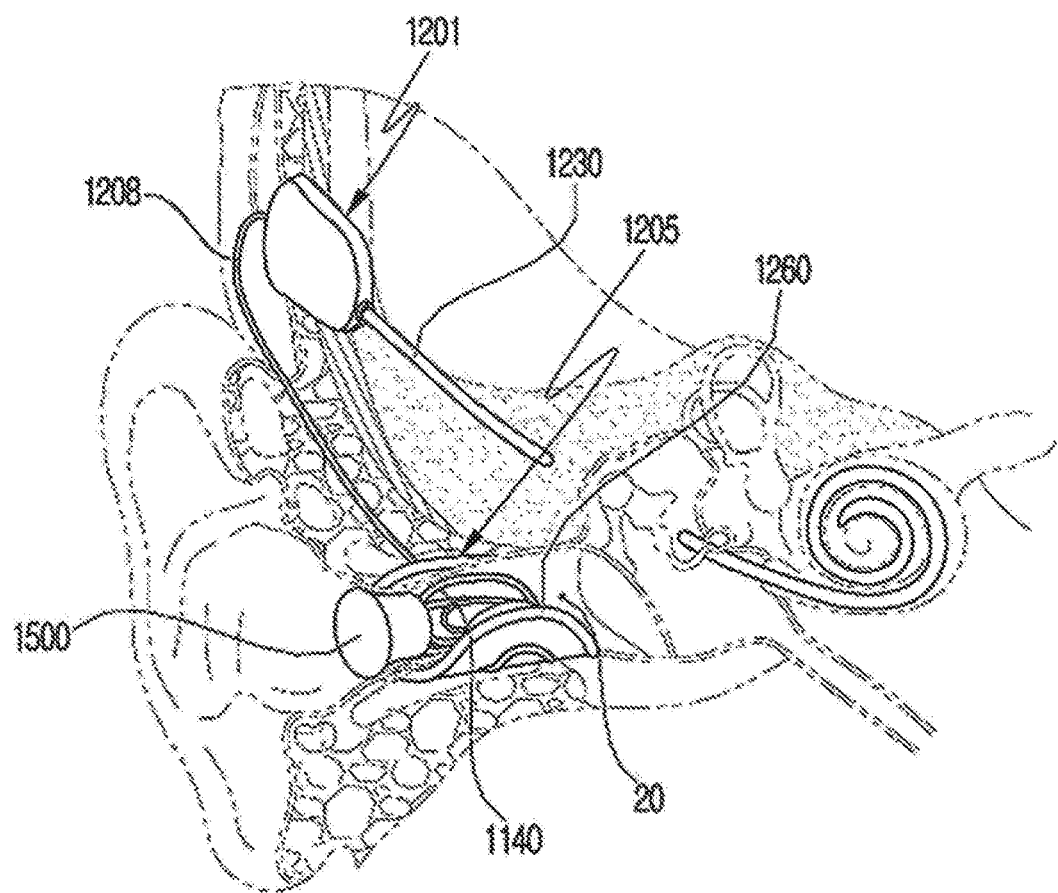
FIG. 5 is an exemplary view illustrating an example in which a human body implant device according to another embodiment of the present invention is applied to the human body.
Figure 6:
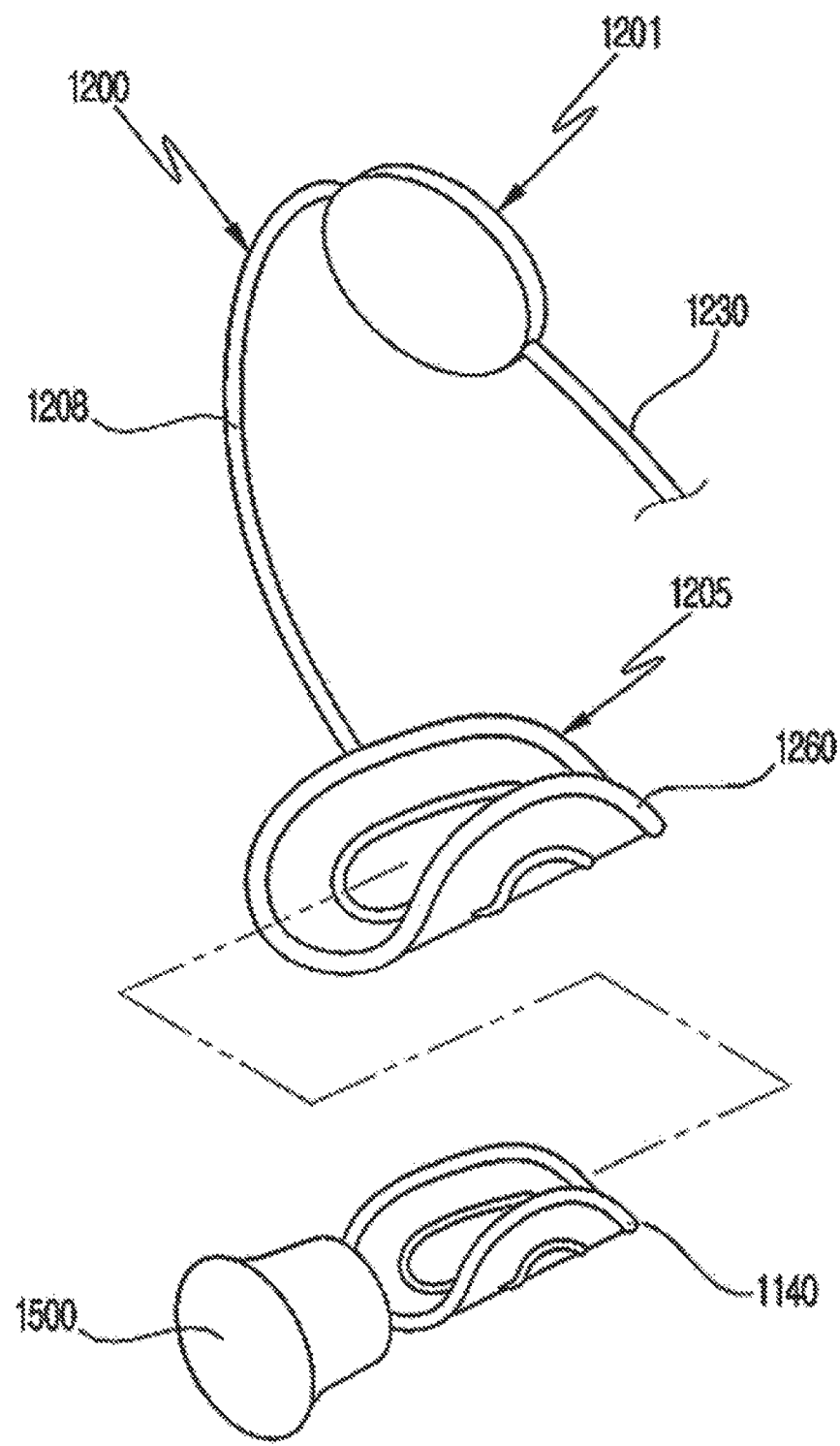
FIG. 6 is an exemplary view illustrating the human body implant device according to the other embodiment of the present invention, mainly on the basis of a first coil and a second coil thereof.

FIG. 5 is an exemplary view illustrating an example in which a human body implant device according to another embodiment of the present invention is applied to the human body, and FIG. 6 is an exemplary view illustrating the human body implant device according to the other embodiment of the present invention, mainly on the basis of a first coil and a second coil thereof.

As illustrated in FIGS. 5 and 6, in the human body implant device according to the present embodiment, a second coil 1260 may be bent to surround an external auditory meatus 20 inside the skin of the external auditory meatus 20.

The second coil 1260 may also have a flat shape that comes into contact with the external auditory meatus 20 inside under the skin of the external auditory meatus 20. Here, the second coil 1260 coming into contact with the external auditory meatus 20 may mean that the second coil 1260 is located in the vicinity of the external auditory meatus 20.

Here, an electrode array 1230 that a first package 1201 of a second unit 1200 includes may be located in the same manner as in the previous embodiment. In the present embodiment, a second package 1205 may be provided at the external auditory meatus 20, the second coil 1260 may be bent to surround the external auditory meatus 20 or have a flat shape to be in contact with the external auditory meatus 20, and a connector 1208 may electrically connect the second package 1205 and the first package 1201.

A first unit may further include an aligner 1500 inserted into the auditory pit, and when insertion of the aligner 1500 into the auditory pit is completed, a first coil 1140 may be located in the external auditory meatus 20. Here, the first coil 1140 may be disposed at a position corresponding to the second coil 1260 so that the first coil 1140 is aligned in place with the second coil 1260. Although the first coil 1140 may be aligned in place with the second coil 1260 in terms of position, embodiments are not limited thereto, and the first coil 1140 may also be aligned in place so that the first coil 1140 is bent to have the same curvature as the second coil 1260. Alternatively, the first coil 1140 may be aligned in place with the second coil 1260 in terms of both the position and curvature.

The first coil 1140 may have a size or shape corresponding to that of the second coil 1260, and may be bent to correspond to the shape of the second coil 1260. For example, when the second coil 1260 is bent to surround the external auditory meatus 20 inside the skin of the external auditory meatus 20, the first coil 1140 may be bent to correspond to the shape of the second coil 1260 or have a flat shape. When the second coil 1260 is formed in a flat shape coming into contact with the external auditory meatus 20 the skin of the external auditory meatus 20, the first coil 1140 may be formed in a flat shape or may be bent to correspond to the shape of the second coil 1260.

The aligner 1500 may include one or more of a sender and a voice processor.

More specifically, the first unit may sense an acoustic signal by the sender of the aligner 1500 and convert the sensed acoustic signal into an electrical signal by the voice processor. The electrical signal generated by the voice processor may be transmitted to the second coil 1260 of the second unit 1200 through the first coil 1140. Therefore, when transmitting power to the second coil 1260, the first coil 1140 may transmit the electrical signal along with power to the second coil 1260. Alternatively, the aligner 1500 may further include a separate transmitter, and may also transmit an electrical signal to the second unit 1200 through the transmitter.

The first unit may include a separate sub-unit (not illustrated) that includes a sender, a voice processor, and a communicator. The sub-unit may sense an acoustic signal, convert the sensed acoustic signal into an electrical signal, and transmit the electrical signal to the aligner 1500 through the communicator.

In a cochlear implant system according to still another embodiment of the present invention, a second coil may also be installed inside an auricle. Also, a first package may be detachably configured outside the auricle. For example, a clip member (not illustrated) coupled to the auricle may be further provided in the first package, or a piercing member (not illustrated) passing through the auricle may be further provided, and in this way, the first package may also be implemented in the shape of an earring.

Figure 7:
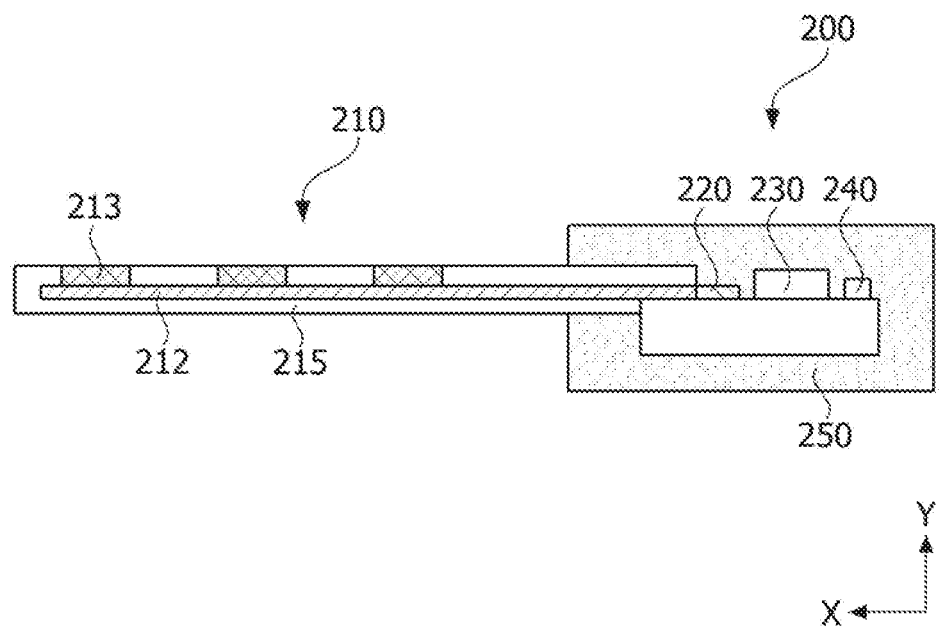
FIG. 7 is a conceptual diagram of a second unit according to an embodiment of the present invention.

FIG. 7 is a conceptual diagram of a second unit according to an embodiment of the present invention.

Referring to FIG. 7, a second unit 200 may be inserted into the skin. As an example, the second unit 200 may be inserted into the subcutaneous layer or implanted in the body. The second unit 200 may receive an electrical signal from the first unit 100 and stimulate auditory nerve fibers in a cochlea.

The second unit 200 may include a receiver 240, a circuit 230 configured to process a signal received from a first unit 100 and generate a stimulation signal, and an electrode array 210 having a plurality of electrodes (not illustrated) configured to stimulate auditory nerve fibers with a current signal in response to the stimulation signal transmitted from the circuit 230.

The receiver 240 and the circuit 230 may be disposed on a support substrate and accommodated inside a housing 250. The housing 250 may be formed of the same polymer material as the support substrate, but embodiments are not necessarily limited thereto.

The electrode array 210 may extend in a first direction (X-axis direction). A length to which the electrode array 210 extends is not particularly limited. The electrode array 210 may have a predetermined length that allows the electrode array 210 to be inserted into the cochlea of the human body and provide stimulation thereto.

A plurality of electrodes 213 may receive a current signal transmitted from the circuit 230 and stimulate auditory nerve fibers in the cochlea, and may also collect, sense, and record a biometric signal from the auditory nerve fibers.

A lead wire 212 may be individually connected to each of the plurality of electrodes 213, and the plurality of lead wires 212 may be connected to a pad 220. The pad 220 may electrically connect the plurality of electrodes 213 and the circuit 230.

Figure 8:
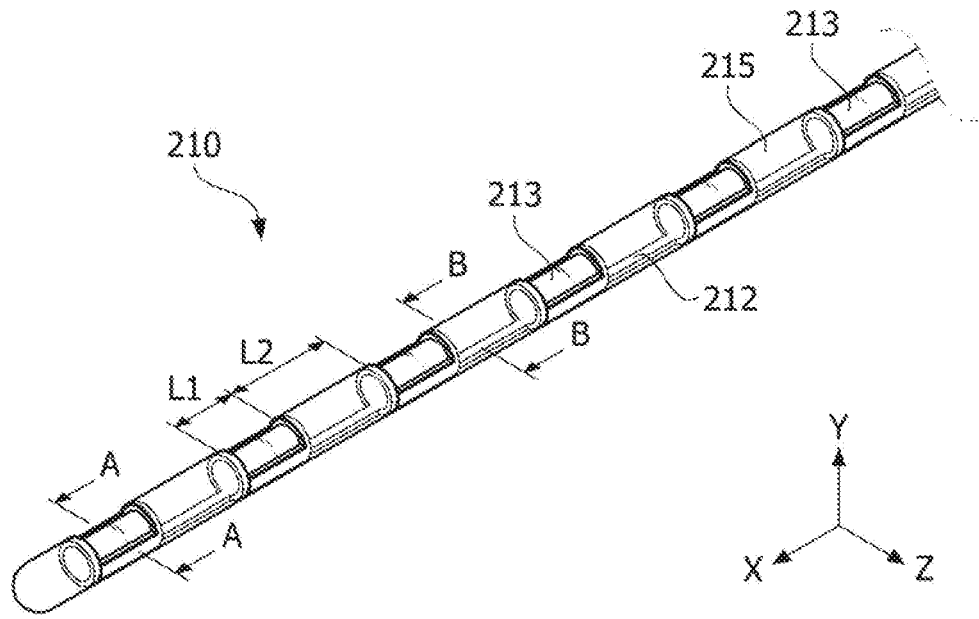
FIG. 8 is a conceptual diagram of an electrode array according to an embodiment of the present invention.
Figure 9:
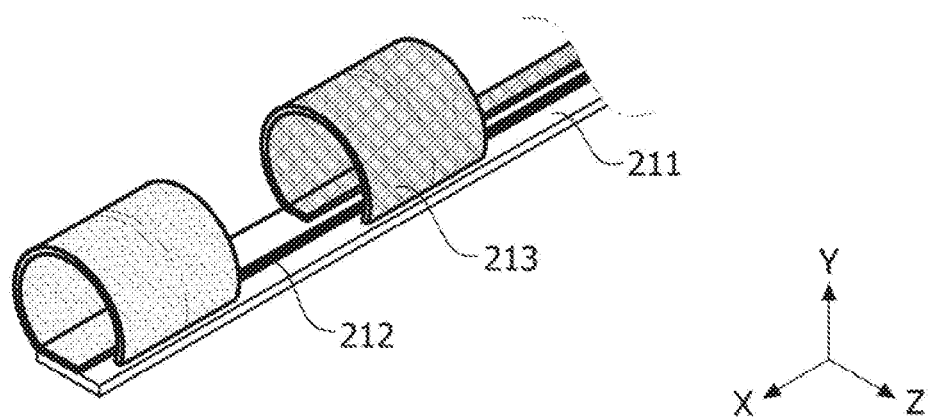
FIG. 9 is a view illustrating an electrode structure.
Figure 10:
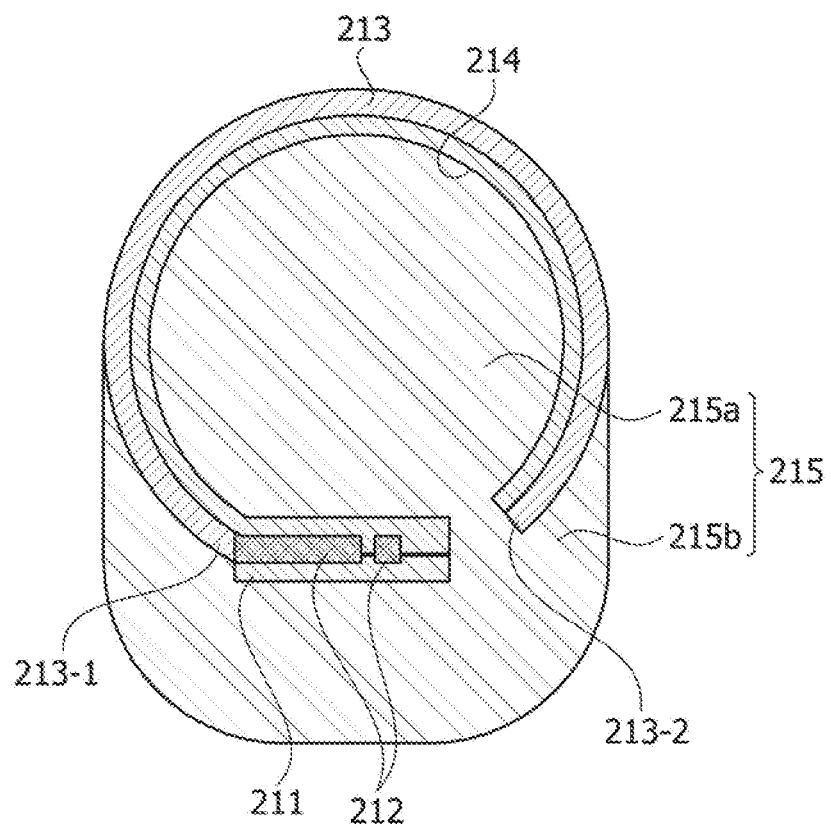
FIG. 10 is a cross-sectional view taken along line A-A in FIG. 8.
Figure 11:
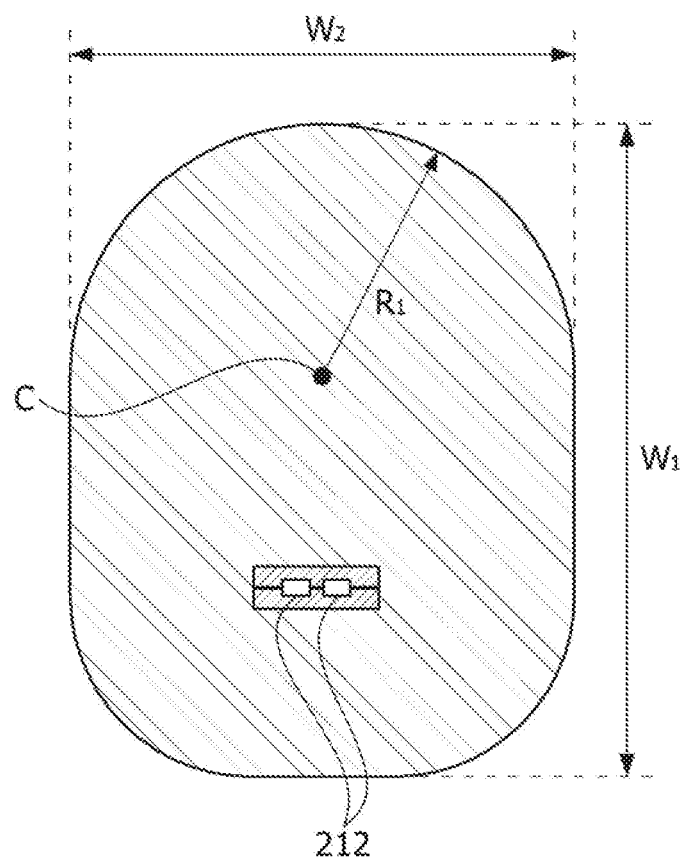
FIG. 11 is a cross-sectional view taken along line B-B in FIG. 8.

FIG. 8 is a conceptual diagram of an electrode array according to an embodiment of the present invention, FIG. 9 is a view illustrating an electrode structure, FIG. 10 is a cross-sectional view taken along line A-A in FIG. 8, and FIG. 11 is a cross-sectional view taken along line B-B in FIG. 8.

Referring to FIGS. 8 and 9, an electrode array 210 according to an embodiment includes a substrate 211 extending in a first direction (X-axis direction), a plurality of lead wires 212 disposed on the substrate 211, a mold member 215 configured to cover the lead wires 212, and a plurality of electrodes 213 disposed at an outer peripheral surface of the mold member 215.

The substrate 211 may have a predetermined width that allows the lead wires 212 to be disposed on the substrate 211. The width of the substrate 211 is not particularly limited. The number of lead wires 212 may vary in accordance with a length of the electrode array 210, and the width of the substrate 211 may be determined in accordance with the number of lead wires 212.

The lead wires 212 may be disposed on the substrate 211 and extend in the first direction (X-axis direction). The plurality of lead wires 212 may be electrically insulated from each other. The lead wires 212 may be patterned on the substrate 211 using a semiconductor process. However, a method of manufacturing the lead wires 212 is not necessarily limited thereto.

The plurality of electrodes 213 may be spaced apart from each other in the first direction and electrically connected to the lead wires 212, respectively. Therefore, the plurality of electrodes 213 may be separately operated. The material of the electrodes 213 is not particularly limited. For example, the electrodes may contain platinum.

A thickness of the electrodes 213 may be in the range of 0.1 μm to 5.0 μm. When the thickness of the electrodes 213 is smaller than 0.1 μm or larger than 5.0 μm (for example, the electrodes 213 are bent in a ring shape), the electrodes 213 may be damaged. The thickness of the electrodes 213 may be equal to that of the lead wires 212, but embodiments are not necessarily limited thereto.

The plurality of electrodes 213 may be disposed at an outer peripheral surface of the mold member 215. As an example, when the mold member 215 is in the shape of a rod, the plurality of electrodes 213 may have a ring shape.

However, embodiments are not necessarily limited thereto, and the plurality of electrodes 213 may have any shape as long as the plurality of electrodes 213 are exposed along an outer surface of the mold member 215 and areas of the plurality of electrodes 213 are widened.

The plurality of electrodes 213 may be bent to surround the mold member 215. That is, the plurality of electrodes 213 may be exposed to the outside of the mold member 215. Therefore, areas of the electrodes 213 exposed to the outside may be relatively widened.

A ratio between widths of a first section L1 in which the electrodes 213 are disposed in the first direction and a second section L2 in which the electrodes 213 are not disposed may be in the range of 1:0.2 to 1:1.5. The first section L1 may be a section in which the electrodes 213 provide stimulation by a current applied thereto, and the second section L2 may be a flexible section.

When the ratio between the widths is smaller than 1:0.2, there is a problem in that the second section is reduced and thus flexibility of the electrode array 210 is decreased, and when the ratio between the widths is larger than 1:1.5, there is a problem in that the areas of the electrodes 213 are reduced and thus it is difficult to provide sufficient stimulation. As an example, when there are sixteen electrodes, the ratio between the widths of the first section and the second section may be 1:1.4, and when there are one hundred electrodes, the ratio between the widths of the first section and the second section may be 1:0.3.

Referring to FIG. 10, the plurality of electrodes 213 may have one end 213-1 that passes through the mold member 215 and is electrically connected to the lead wire 212, and the other end 213-2 fixed to the mold member 215. That is, since the both ends 213-1 and 213-2 of the electrodes 213 are fixed to the mold member 215, the shape of the electrodes 213 may be maintained. 10% to 30% of the entire length of the electrodes 213 may be fixed to the inside of the mold member 215 for the shape of the electrodes 213 to be maintained, but embodiments are not necessarily limited thereto.

The mold member 215 may serve to support inner portions of the plurality of electrodes 213. A flexible material may be selected as a material of the mold member 215 for the mold member 215 to be inserted into the cochlea of the human body. As an example, the mold member 215 may be formed of a silicone material, but embodiments are not necessarily limited thereto.

The mold member 214 may include a first mold member 215a disposed inside the electrodes 213, and a second mold member 215b disposed outside the electrodes 213. The first mold member 215a may be defined as a region surrounded by the electrodes 213, and the second mold member 215b may be defined as a region that surrounds the electrodes 213. Both of the ends 213-1 and 213-2 of the electrodes 213 may be fixed by being coupled between the first mold member 215a and the second mold member 215b.

The first mold member 215a and the second mold member 215b may be formed of the same material, but embodiments are not necessarily limited thereto. A curvature of an outer diameter of the first mold member 215a and a curvature of an outer diameter of the second mold member 215b may also be different. The first mold member 215a may have a curvature that corresponds to an inner diameter of a ring structure.

A cover 214 may be disposed on the substrate 211 and protect the lead wires 212. The substrate 211 may have the lead wires 212 patterned thereon and have a flat surface.

The cover 214 may include a flat portion disposed to correspond to the substrate 211, and a curvature portion disposed between the electrodes 213 and the first mold member 215a. According to an embodiment, the cover 214 may be disposed between the electrodes 213 and the first mold member 215a. When the cover 214 is a thermoplastic resin, the cover may be thermoformed in advance prior to an injection of the first mold member 215a so that an adhesive strength between the cover 214 and the first mold member 215a is improved.

Referring to FIG. 11, at a portion of the electrode array 210 in which the electrodes 213 are not disposed, only the lead wires 212 may be disposed between the substrate 211 and the cover 214. That is, the section in which the electrodes 213 are not disposed may be a relatively flexible section.

A thickness W1 of the electrode array 210 may be in the range of 0.2 mm to 0.8 mm, and a width W2 of the electrode array 210 may be in the range of 0.2 mm to 0.8 mm. The thickness and the width may be the same. Here, the maximum radius R1 from the center C1 of the cross-section may be in the range of 0.2 mm to 0.8 mm. When the maximum radius R1 is smaller than 0.2 mm, the electrode array 210 may not maintain sufficient contact with an inner wall of the cochlea and thus signal transmission efficiency may be lowered, and when the maximum radius R1 is larger than 0.8 mm, due to a large diameter of the electrode array 210, it may become difficult to insert the electrode array 210 into the cochlea, and flexibility of the electrode array 210 may be significantly reduced.

FIGS. 12 to 21 are views showing a process of manufacturing an electrode array.

Referring to FIG. 12, a plurality of lead wires 212a, 212b, and 212c and a plurality of electrodes 213a, 213b, and 213c may be patterned on a substrate 211. A patterning method is not particularly limited. Any patterning method that is generally used in a semiconductor process may be applied. As an example, patterning may be performed by performing selective etching using a mask.

The substrate 211 may be formed of a liquid crystal polymer, but embodiments are not necessarily limited thereto. Any material may be applied as the material of the substrate 211 as long as the material is flexible and allows patterns to be easily formed on the substrate 211.

Referring to FIG. 13, a cover 214 may be laminated on the substrate 211. The cover 214 may be formed of the same material as the substrate 211. The plurality of lead wires 212 and the plurality of electrodes 213 may be laminated between the substrate 211 and the cover 214. Any general lamination method may be applied as the laminating method.

Figures 14A, 14B:
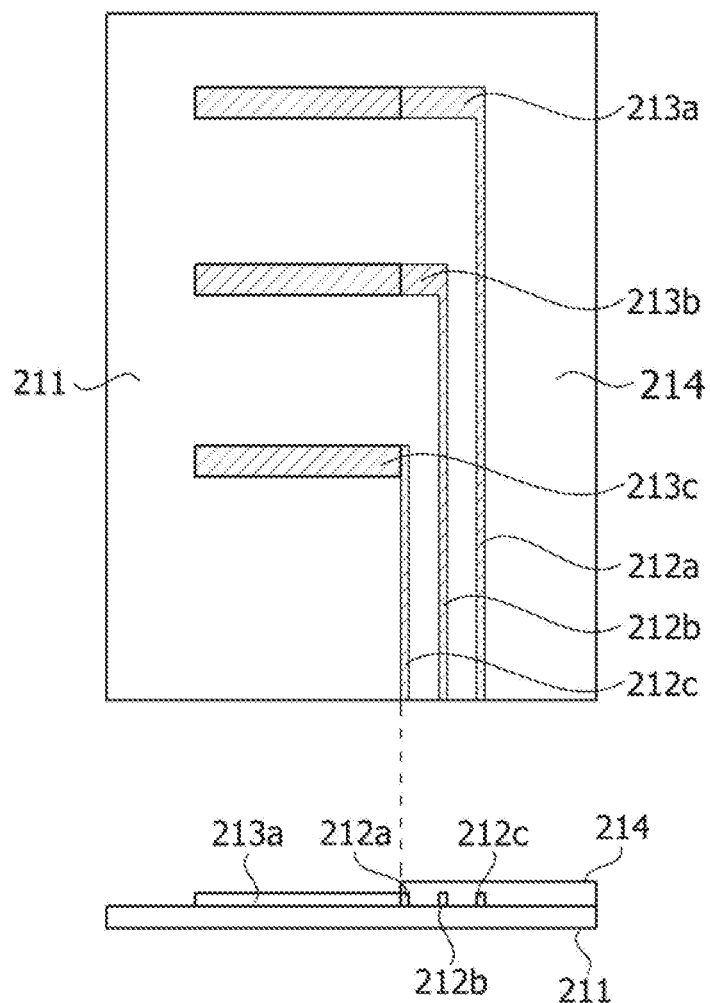

Referring to FIG. 14, a portion of the cover 214 may be incised so that the plurality of electrodes 213 are partially exposed. As an example, portions of electrodes may be exposed using laser scribing, and the remaining portions may then be removed using oxygen plasma etching. Here, areas in which the plurality of electrodes 213 are exposed may be the same. Therefore, when the plurality of electrodes 213 are bent in a ring shape, areas thereof may be the same.

Referring to FIG. 15, outer boundaries may be cut off to manufacture an electrode structure P. A cutting method is not particularly limited. Here, the substrate 211 may be left unchanged at rear surfaces of the plurality of electrodes 213.

Figure 16:
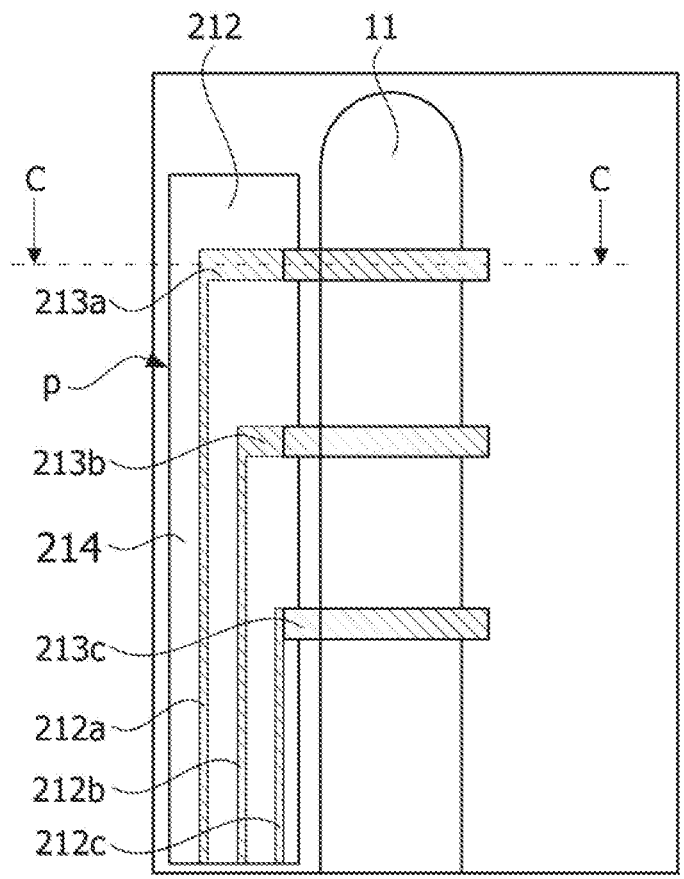
Figure 17:
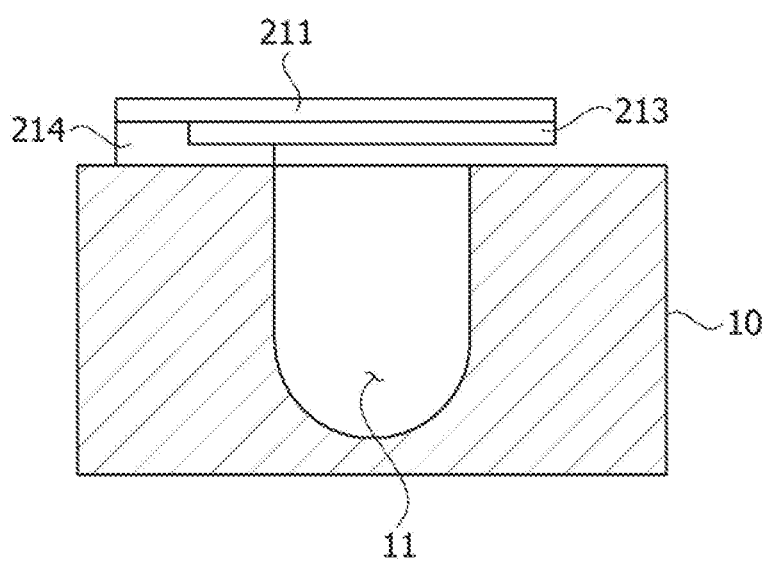
Figure 18:
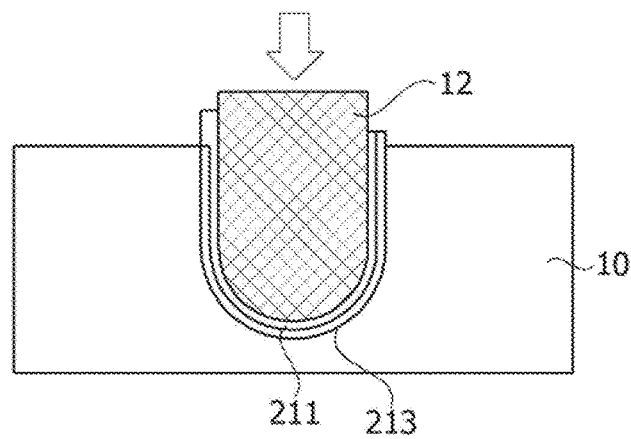

Referring to FIGS. 16 to 18, the electrode structure P may be disposed on a forming mold 10, and a portion of the electrode structure P corresponding to a groove 11 of the forming mold may be pressed with a press 12 so that the electrode structure P is initially bent. Here, the electrodes 213 of the electrode structure P may be bent in a circular shape along an inner surface of the groove 11. However, embodiments are not necessarily limited thereto, and the shape in which the electrodes 213 are bent may vary in accordance with the shape of the groove 11.

Figure 19:
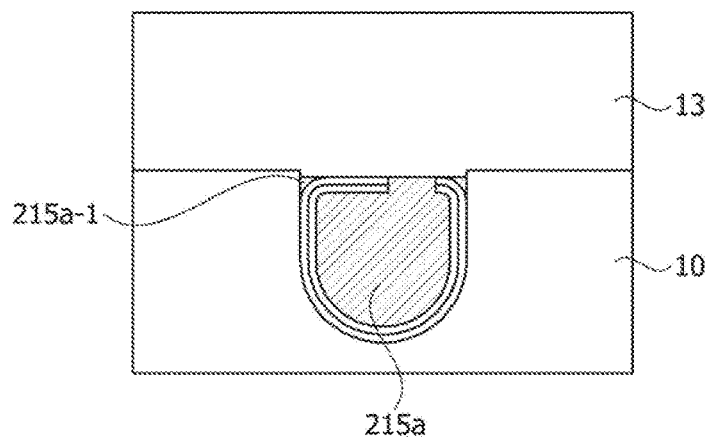

Referring to FIG. 19, a first injection cover 13 may be disposed on the forming mold 10, and a molding resin may be injection-molded. Therefore, the firstly-bent electrodes 213 may be filled with the first mold member 215a. Here, a gap 215a-1 between bent portions may also be filled with resin.

Figure 20:
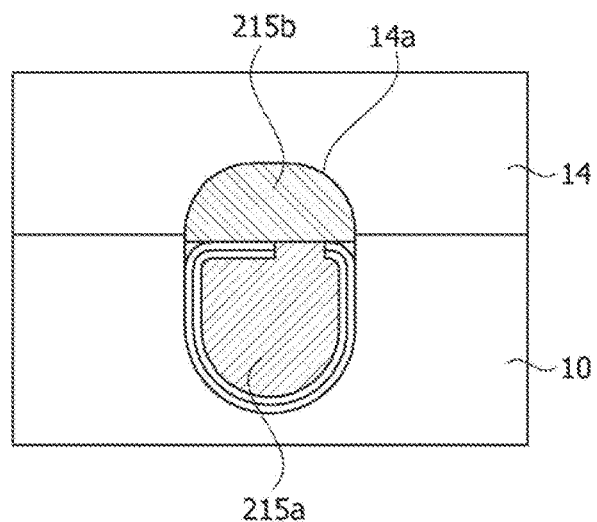
Figure 21:
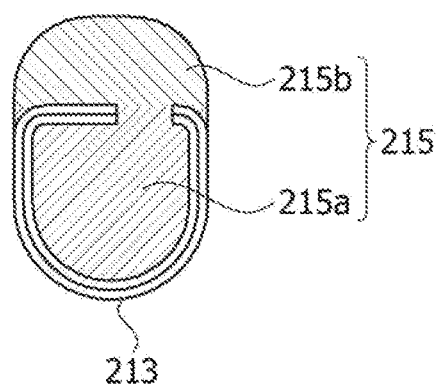

Referring to FIGS. 20 and 21, a second injection cover 14 having a groove 14a may be disposed on the forming mold 10, and a resin may be injection-molded again. Therefore, outer surfaces of the electrodes 213 may be filled with the second mold member 215b.

According to an embodiment, through the two sessions of injection molding, the first mold member 215a may be formed inside the electrodes 213, and the second mold member 215b may be formed outside the electrodes 213. The shape of the electrodes 213 may be fixed by the first mold member 215a and the second mold member 215b.

Figure 22:
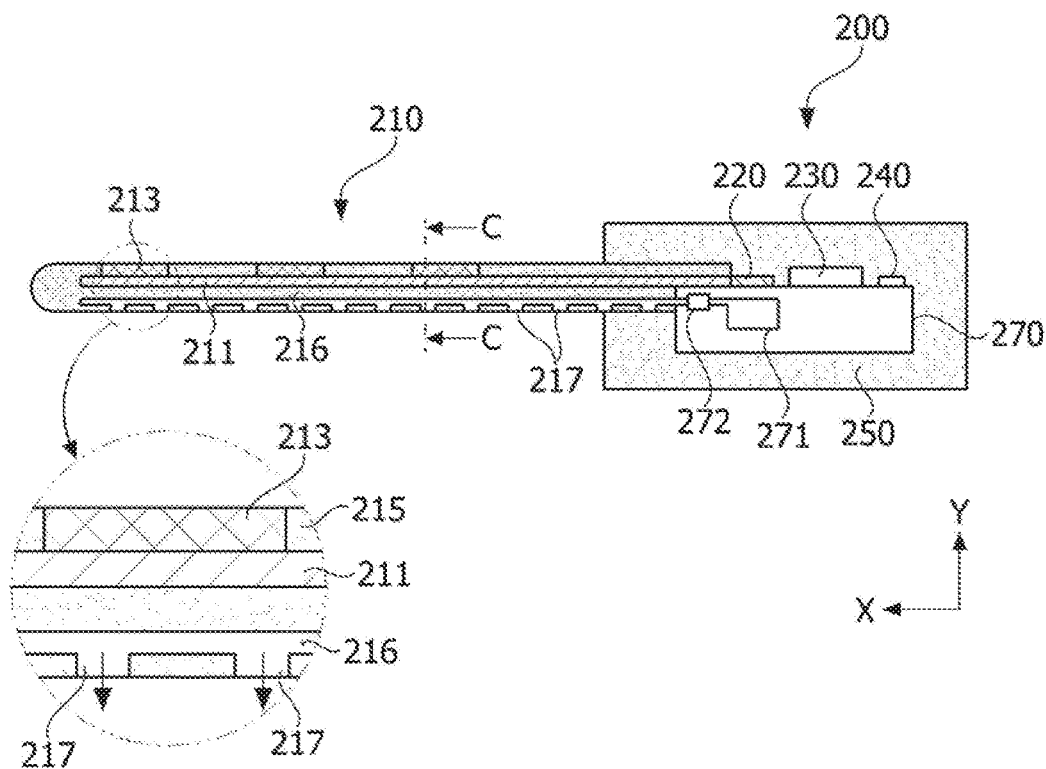
FIG. 22 is a conceptual diagram of a second unit according to another embodiment of the present invention.
Figure 23:
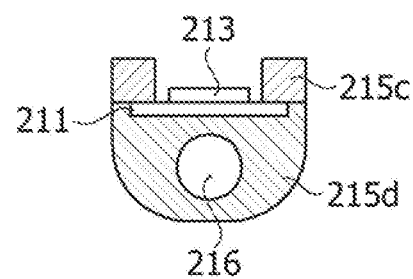
FIG. 23 is a cross-sectional view taken along line C-C in FIG. 22.
Figure 24:
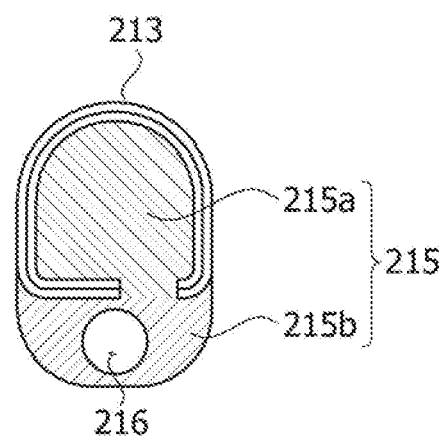
FIG. 24 is a modified example of FIG. 23.

FIG. 22 is a conceptual diagram of a second unit according to another embodiment of the present invention, FIG. 23 is a cross-sectional view taken along line C-C in FIG. 22, and FIG. 24 is a modified example of FIG. 23.

Referring to FIG. 22, a second unit 200 may be inserted into the skin. As an example, the second unit 200 may be inserted into the subcutaneous layer, or may be implanted in the body. The second unit 200 may receive an electrical signal from a first unit and stimulate auditory nerve fibers in the cochlea.

The second unit 200 may include a receiver 240, a circuit 230 configured to process a signal received from the first unit and generate a stimulation signal, and an electrode array 210 having a plurality of electrodes 213 configured to stimulate auditory nerve fibers with a current signal in response to the stimulation signal transmitted from the circuit 230.

The receiver 240 and the circuit 230 may be disposed on a support plate and accommodated inside a housing 250. The housing 250 may be formed of the same polymer material as the support substrate, but embodiments are not necessarily limited thereto.

The electrode array 210 may extend in a first direction (X-axis direction). The length to which the electrode array 210 extends is not particularly limited. The electrode array 210 may have a predetermined length that allows the electrode array 210 to be inserted into the cochlea of the human body and provide stimulation thereto.

The plurality of electrodes 213 may receive a current signal transmitted from the circuit 230 and stimulate auditory nerve fibers in the cochlea, and may also collect, sense, and record a biometric signal from the auditory nerve fibers.

A pad 220 may be connected to an end of a lead wire and electrically connect the plurality of electrodes 213 and the circuit 230.

The electrode array 210 may include a flow path 216 extending in a longitudinal direction. The electrode array 210 may include a plurality of holes 217 configured to communicate with the flow path 216.

The electrode array 210 may be inserted into the cochlea of the human body to deliver stimulation. Here, drugs delivered through the flow path 216 of the electrode array 210 may be injected into the cochlea through the holes 217.

As needed, the drugs may solely be injected into the cochlea without the electrodes being inserted thereinto.

The drugs may serve to suppress or mitigate damage to tissues of the cochlea upon insertion of the electrode array 210 into the cochlea. The drugs may also serve to treat hearing loss. As an example, the drugs may be steroids, but embodiments are not necessarily limited thereto.

A diameter of the flow path 216 may be in the range of 0.1 mm to 0.5 mm. When the diameter is smaller than 0.1 mm, the drugs may not be injected to an end of the electrode array due to an internal pressure of the flow path 216, and when the diameter is larger than 0.5 mm, there is a problem in that an overall diameter of the electrode array 210 has to be increased.

A method of injecting the drugs is not particularly limited. As illustrated, a drug storage 271 may be disposed inside a second unit, and the drugs may be injected into the flow path 216 by an osmotic pump 272 or the like.

A position of the drug storage 271 is not particularly limited. As an example, the drug storage 271 may be disposed above or beside a support plate 270, or may be disposed at an appropriate position that allows the drugs to be regularly charged into the drug storage 271 using a syringe or the like. In this case, there is an advantage in that the drugs can be regularly charged into the drug storage 271 using the syringe or the like without removing the second unit from the human body.

As another embodiment, the drugs may be delivered in a state of having been inserted into a flow path 216 of an electrode array 210 in advance. Therefore, after the human body implant device is inserted into the human body, the drugs may be gradually melted due to internal body temperature and then injected into the body.

As still another embodiment, a flow path 216 may also be connected to an inlet (not illustrated) provided outside a second unit. In this case, an operator may inject the drugs into the inlet using the syringe or the like after insertion of the electrode array 210 is completed.

Referring to FIG. 23, an electrode array 210 may include a substrate 211, an electrode 213 disposed on the substrate 211, a lower mold member 215d, and an upper mold member 215c. The flow path 216 may be formed in a lower mold member. Even in a structure of an electrode array 210 illustrated in FIG. 24, a flow path 216 may be formed in a second mold member 215b.

According to an embodiment, there is an advantage in that the flow path 216 and the holes 217 may be easily formed upon forming a mold member. Therefore, there is an advantage in that a member for separately injecting drugs may be omitted.

The description of the present invention given above is merely illustrative, and those of ordinary skill in the art to which the present invention pertains should understand that the present invention may be easily modified to other specific forms without changing the technical spirit or essential features of the present invention.

Therefore, the embodiments described above should be understood as illustrative in all aspects instead of limiting. For example, each element described as above a single element may be embodied in a distributed form, and likewise, elements described above as distributed elements may be embodied in a combined form.

The scope of the present invention is indicated by the claims below, and the meaning, scope, and all changes or modifications derived from concepts equivalent to the claims should be interpreted as belonging to the scope of the present invention.

What is claimed is:

1. A human body implant device comprising:
a first unit including a first coil; and
a second unit configured to communicate with the first unit,
wherein the second unit includes:
a second package including a second coil configured to receive power or an electrical signal from the first coil;
a first package configured to generate a stimulation signal in response to the electrical signal;
a connector configured to electrically connect the first package and the second package; and
a first cover configured to package the first package, the second package, and the connector,
a circuit configured to process the electrical signal and generate the stimulation signal; and
an electrode array configured to apply a current signal in response to the stimulation signal,
wherein the electrode array includes:
a substrate extending in a first direction and comprising a first surface and a second surface opposite to the first surface;
a plurality of lead wires disposed on the first surface of the substrate;
a plurality of electrodes connected to the plurality of lead wires and extending toward a second direction perpendicular to the first direction;
a second cover disposed on the first surface of the substrate to cover the plurality of lead wires; and
a mold member configured to cover the substrate, the plurality of electrodes, and the second cover,
wherein each of the plurality of electrodes comprises an exposed portion disposed on an outer peripheral surface of the mold member,
a first end portion inserted in the mold member and electrically connected to the plurality of lead wires, and
a second end portion inserted in the mold member, and
wherein an area in which the plurality of electrodes is covered with the second cover increases toward the first direction.

2. The human body implant device of claim 1, wherein the connector electrically connects the second coil and the circuit.

3. The human body implant device of claim 1, wherein the connector includes a wire configured to electrically connect the second coil and the first circuit, and the cover is coated onto the wire.

4. The human body implant device of claim 1, wherein the first unit includes:
a sender configured to sense an acoustic signal; and
a voice processor configured to convert the acoustic signal into an electrical signal.

5. The human body implant device of claim 1, wherein the plurality of electrodes are disposed to be spaced apart from each other in the first direction.

6. The human body implant device of claim 5, comprising a first section in which the electrodes are disposed, and a second section in which the electrodes are spaced apart from each other in the first direction,
wherein a ratio between widths of the first section and the second section in the first direction is in a range of 1:0.2 to 1:1.5.

7. The human body implant device of claim 1, wherein the mold member includes:
a flow path disposed therein and extending in the first direction; and
a plurality of holes connected to the flow path.

* * * * *